United States Patent [19]

Steuer

[11] 4,239,048
[45] Dec. 16, 1980

[54] CARDIOTACHOMETER USING AUTOCORRELATION TECHNIQUES

[75] Inventor: Robert R. Steuer, Salt Lake City, Utah

[73] Assignee: Multitronics Corporation, Salt Lake City, Utah

[21] Appl. No.: 9,823

[22] Filed: Feb. 6, 1979

[51] Int. Cl.³ ............................................. A61B 5/02
[52] U.S. Cl. ..................................... 128/666; 128/690
[58] Field of Search .............. 128/666, 669, 690, 706, 128/707

[56] References Cited

U.S. PATENT DOCUMENTS

| | | | |
|---|---|---|---|
| 3,202,149 | 8/1965 | Emmons | 128/706 |
| 3,230,951 | 1/1966 | Teschner | 128/666 |
| 3,717,140 | 2/1973 | Greenwood | 128/689 |
| 3,858,574 | 1/1975 | Page | 128/666 |
| 3,908,636 | 9/1975 | Page | 128/666 |
| 3,908,640 | 9/1975 | Page | 128/689 |
| 4,009,708 | 3/1977 | Fay, Jr. | 128/690 |
| 4,015,595 | 4/1977 | Benjamin, Jr. | 128/666 |
| 4,030,483 | 6/1977 | Stevens | 128/666 |
| 4,058,118 | 11/1977 | Stupay et al. | 128/690 |
| 4,086,916 | 5/1978 | Freeman et al. | 128/663 |
| 4,090,504 | 5/1978 | Nathan | 128/670 |
| 4,096,854 | 6/1978 | Perica et al. | 128/690 |
| 4,120,294 | 10/1978 | Wolfe | 128/706 |
| 4,120,296 | 10/1978 | Prinz | 128/690 |

*Primary Examiner*—Kyle L. Howell
*Attorney, Agent, or Firm*—Fleit & Jacobson

[57] ABSTRACT

A cardiotachometer for indicating heart rate of a user in beats per minute. The cardiotachometer comprises a sensor, placed on the body of the user, for producing an electrical signal indicative of the heart rate of the user. Circuitry is provided for converting the electrical signal into first and second digital signals. 60/t computation circuitry responds to the first and second digital signals and produces a third digital signal having a varying frequency representative of the number of heart beats per minute. An up-counter converts the third digital signal into a plurality of binary number signals, each bit of which is stored in a series of shift registers. A compare using a plurality of exclusive OR gates, compares each of the stored binary number signals with the most recent binary number signal, from the up-counter, to determine if a plurality of compared signals are within a predetermined percentage of each other. Finally, a display is provided for displaying the most recent binary number signal, when the plurality of compared signals are within the predetermined percentage of each other. Further provision is made for display of both elapsed time and time of day.

24 Claims, 8 Drawing Figures

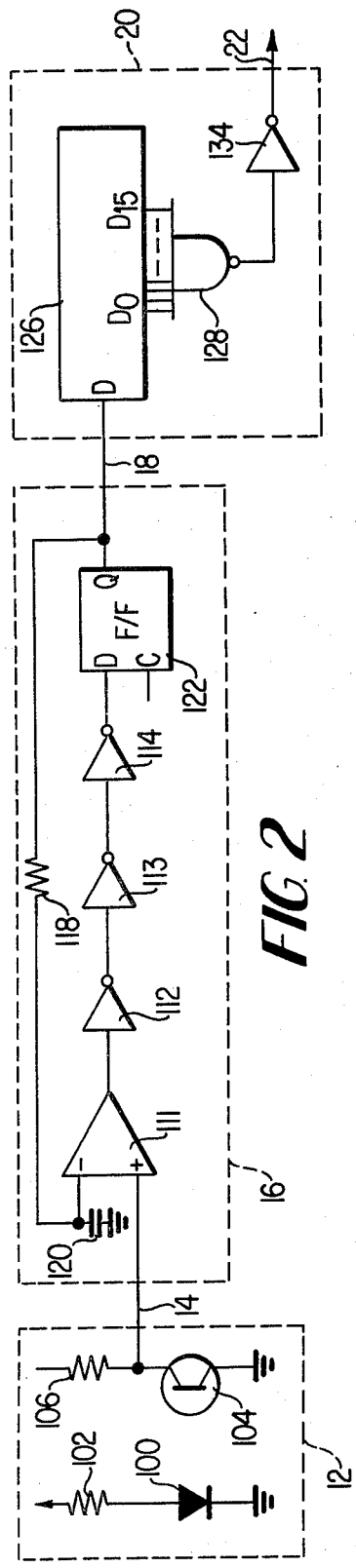
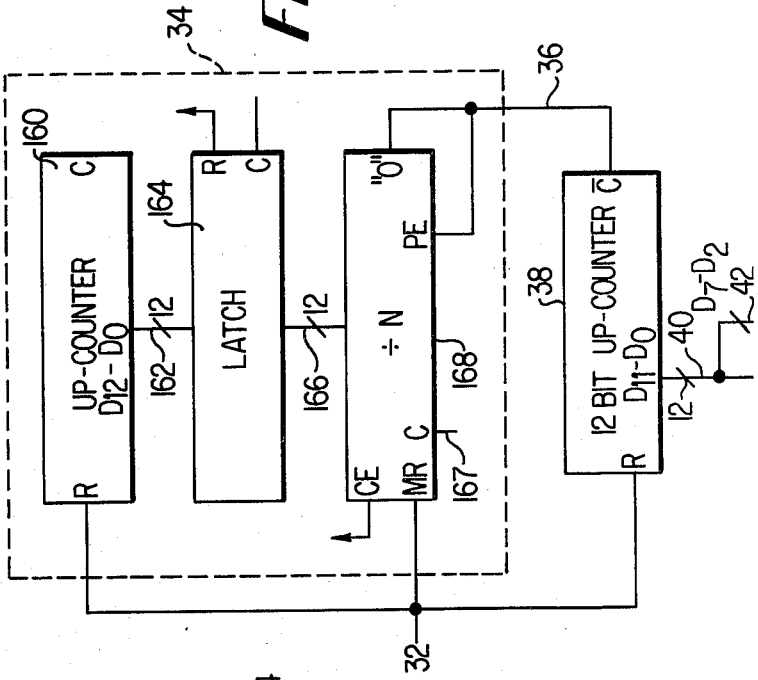
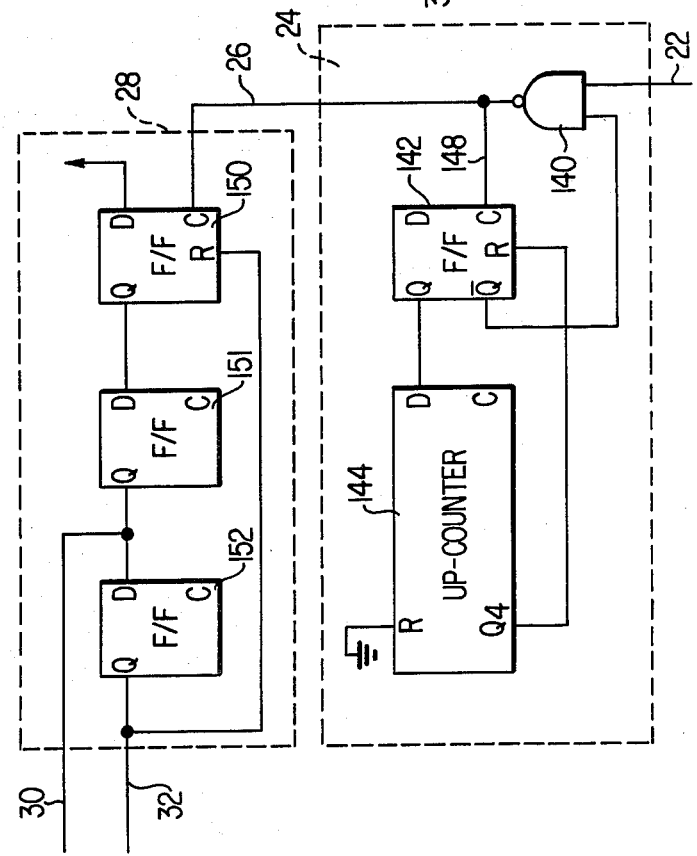
FIG. 2
FIG. 4
FIG. 3

CARDIOTACHOMETER USING AUTOCORRELATION TECHNIQUES

BACKGROUND OF THE INVENTION

1. Field of the Invention

The present invention relates to pulse monitors with visual readout, in general, and to a cardiotachometer which performs a comparison between selected heartbeat intervals such that when any plurality of the intervals are within a predetermined percentage of each other, the plurality of intervals are averaged, read out and held in the display until the next update.

2. Description of the Prior Art

Heart rate is the basic parameter used to evaluate and determine the condition of the human body. In carrying out its action, the heart produces three wave complexes, designated as P, QRS, and T, each of which corresponds to a particular electrical event within the heart. It has long been known that the R wave produces the greatest electrical activity, and for this reason the R—R interval has been used as a way of measuring the time between heartbeats. By knowing the time between heartbeats, it is easy to determine the number of beats per minute.

The contraction, or period of contraction, of the heart, is referred to as a systole. It coincides with the interval between first and second heart sounds, during which blood is forced into the aorta and the pulmonary trunk. In the same way the R—R interval may be used as a way of measuring the time between heartbeats, the interval between systoles may be used for the same purpose.

During a systole, the heart contracts and forces blood through the arteries, which respond by expanding. Thus, a systole may be detected by placing an appropriate transducer or sensor against any of the well known pressure points on the human body or in an area where blood flow is occurring.

The transducer may be in the form of a pressure transducer, such as a piezoelectric crystal or a phototransducer in the form of a light emitting diode and a photocell.

There are any number of prior art pulse monitors which detect the R—R interval or the systolic rate, compute the heart rate in beats per minute and, then, display every update as an instantaneous beat-by-beat readout. An undesirable feature of this procedure is that movements of the transducer by the user are not distinguished from actual heart pulses by the transducer and thus a false reading occurs. Another cause of false readings is the detection by the transducer of normal respiratory fluctuation or psychomotor responses. These readings manifest themselves in a constantly changing display.

To avoid such false readings, electronic pulse rate measuring devices have been designed to average the time interval over 4, 8, 10, or 16 beats to get an average heart beat. Each of these averaging techniques has its own drawback. In the case of the 4 beat average, there is still some jumping of the readout. The problem with the 8, 10 or 16 beat average is the long time interval between updates. Probably the most important drawback found in all averaging systems is that any error occurring during the period under consideration is also averaged into the final readout.

There is thus a need for a cardiotachometer or a pulse monitor which produces a continuous update and display, and which is not plagued by the problems of inconsistent readout, and the introduction of error from any source, such as, muscle tremor, poor sensor contact, and inappropriate use, to name a few. The present invention is directed toward filling that need.

SUMMARY OF THE INVENTION

In accordance with the subject invention, there is provided a miniature, totally self-contained cardiotachometer to be worn or held by a user for numerically displaying a continuous readout of the user's heart beat rate. The device, which may be housed in a wrist watch or a compact hand-held unit, basically comprises a sensor in the form of a light emitting diode and a photocell which is placed on the finger of the user. The photocell responds to the variations in light intensity reflected off the capillary bed within the finger to produce an analog voltage signal representative of the systolic beats. This signal is received by a slope detector where it is amplified and converted into a digital signal.

The digital signal is delayed for a predetermined time and then fed into a pulse shaper to produce a pair of clean pulse trains. One pulse train is used to reset an up-counter and a 60/t computation block, while the other pulse train is used to latch data within the 60/t computation block.

The 60/t computation circuitry produces an output signal which has a frequency representative of the heart rate in beats per minute. This signal is used to cause an up-counter to produce a binary number equal to the number of beats per minute. This number is fed to a latch and held.

The binary number from the up-counter, with the two least significant bits excluded, is simultaneously fed to a comparator and a series of holding registers.

In the preferred embodiment the holding registers typically comprise a plurality of 10-bit shift registers, one being associated with each binary bit from the up-counter. The binary numbers from the up-counter are placed into the holding registers on a first-in first-out (FIFO) basis. Thus, the eleventh number placed into the holding registers will replace the first number previously stored therein. If the bits of the current number from the up-counter are the same as the bits of one of the numbers in the holding registers, a compare signal is issued and fed to a detect up-counter. This comparison continues with the remaining numbers stored in the holding registers. When at least one more valid comparison is made, the detect up-counter is advanced to produce a latch signal. The latch responds to this signal by causing the data stored therein to be transferred to a display where the data is converted into an array of integers in eye readable format.

Provision is also made for an elasped time indicator and a conventional time-of-day clock, each of which have their readout on the same display as the cardiotachometer.

It is thus an object of the present invention to provide a cardiotachometer for producing a numerical indication of pulse rate with an extremely high degree of accuracy.

It is another object of the present invention to provide a totally unified, self-contained, sensor-electronic-display pulse monitor.

It is still an object of the present invention to provide a simple, inexpensive pulse monitor not plagued by readout error.

It is yet an object of the present invention to provide a pulse monitor not plagued by movements of the sensor at the detection site by the user.

It is a further object of the present invention to provide a pulse monitor in which beat-by-beat read unsteadiness, due to normal respiratory fluctuation or psychomotor responses, is ameliorated.

Additional objects of the present invention will become apparent from a reading of the appended specification and claims in which preferred but not necessarily the only forms of the invention will be described in detail, taken in connection with the drawings accompanying and forming a part of the application.

BRIEF DESCRIPTION OF THE DRAWINGS

FIG. 2 is block circuit diagram showing examples of the sensor, the modulator and the slope detector;

FIG. 3 is a block circuit diagram showing examples of the time delay and the pulse shaper;

FIG. 4 is a block circuit diagram showing examples of the 60/t computation circuit and the up-counter;

DETAILED DESCRIPTION OF THE DRAWINGS

Figure 1:
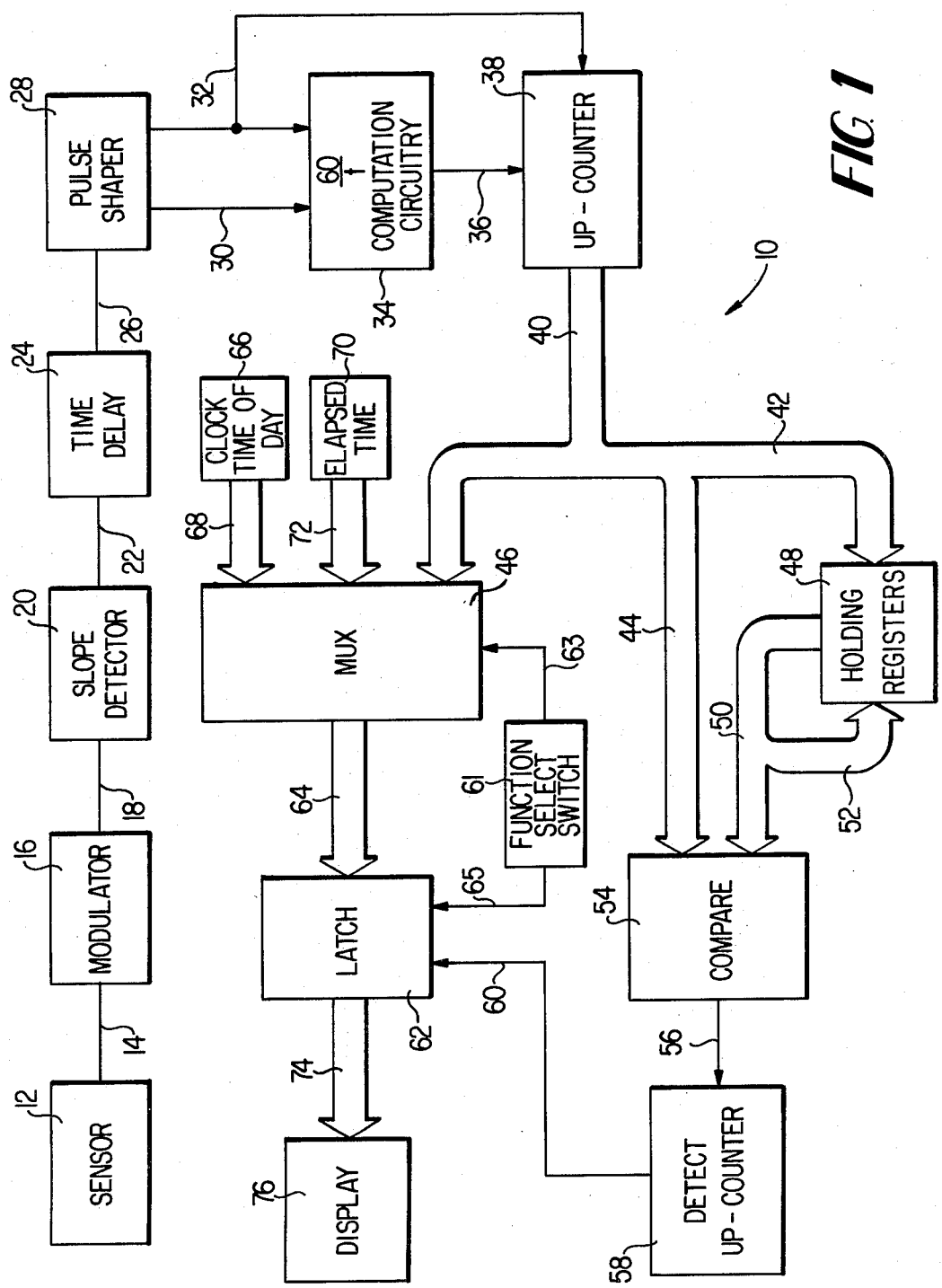
FIG. 1 is a functional block diagram for a preferred embodiment of the subject invention.

With reference to FIG. 1, the cardiotachometer of the subject invention is generally noted as 10. In a preferred embodiment of the subject invention, the cardiotachometer 10 is a totally self-contained unit in the form of a wrist watch or a hand-held device.

A sensor 12, which may be a conventional pressure transducer or a light emitting diode/photocell combination, measures the systolic beats of the user. In the case of the wrist watch embodiment, the beats are sensed at the wrist of the user in a conventional manner. In the case of the hand held device, the beats are sensed through a finger of the user in a conventional manner. The electrical signal produced by the sensor is fed into a modulator 16 via leads 14. The modulator 16 converts the incoming signal into a digital signal for interpretation by the slope detector 20. The output of the slope detector 20 appears on line 22 and is fed to a time delay 24. The output of the time delay appearing on leads 26 is fed to a pulse shaper 28 which produces two pulse trains on lines 30 and 32.

The signals appearing on lines 30 and 32 are fed into 60/t computation circuitry 34. The signals on lines 30 and 32 cause the 60/t circuit 34 to produce at its output 36, a digital signal having a frequency equal to the number of heart beats per minute.

An up-counter 38 responds to the signal on line 36 by producing an output signal 40 which is a digital representation in binary form of the number of beats per minute. The signal appearing on line 32 is used to reset the up-counter 38 between detected beats.

The output of the up-counter is typically a 12-bit number, D11–D0, which is fed to a multiplexer 46. The multiplexer 46 also receives the output of a time of day clock 66 on lines 68, and an elapsed time indicator 70 on lines 72.

At the same time, 6 bits, D7–D2, from the output of the up-counter are fed to holding registers 48 on lines 42 and to a compare 54 via lines 44. The holding registers 48 typically comprise a series of 10-bit shift registers, although shift registers having a capacity for a greater or lesser number of bits can be used. The holding registers are clocked at a rate such that the entire contents of the registers are presented to the compare 54 before the output of the up-counter is changed. The output of the holding registers 48 is also reinserted into the registers on a first-in first-out basis, along with the output of the up-counter so that the oldest piece of data is replaced by the output of the up-counter.

The compare 54 contrasts the data from the up-counter 40, appearing on lines 44, with the data samples contained in the holding registers 48, appearing on lines 50. When the bits on line 44 are the same as the bits on line 50, the compare 54 issues a compare signal on line 56.

The detect up-counter which is typically a conventional up-counter, is caused to advance or count one unit by the compare signal 56. When the detect up-counter has advanced at least two, but typically three, units, a latch pulse is issued on line 60.

A function select switch 61, which is typically a multiposition switch or a series of push button switches located external to the device, provides a means for selecting between three functions for display, namely, time of day, elapsed time, or heart rate. When heart rate is selected the multiplexer 46 feeds the output of the up-counter 38 to the latch 62. The signal appearing on line 60 from the detect up-counter 58 causes the latch 62 to issue appropriate signals on lines 74 to cause a conventional display 76 to display in eye readable form the heart rate of the user in beats per minute.

When the user wishes to display the time of day or the elapsed time, the function select switch 61 also activates the latch 62 to produce the appropriate display in eye readable format on display 76.

A detailed description of the sensor 12, the modulator 16, and the slope detector 20 will now be presented with reference to FIG. 2. The sensor 12 comprises a light emitting diode (LED) 100 in series with a resistor 102 between a source of potential Vcc and ground. There is also provided a photocell in the form of a phototransistor 104 in series with a resistor 106 between a source of potential Vcc and ground. The photocell senses the light from the LED bouncing off the capillary bed within the skin of the wearer as a beam of varying intensity caused by the systolic beats. The photocell responds by producing a varying voltage which is fed into the positive term of a comparator 110.

The output of the comparator 110 is fed to the D input of flip-flop 122 via inverters 112 through 114. The flip-flop 122 produces a pulse train at its Q output which is fed back through resistor 118 to the negative input of the comparator 110. A capacitor 120 is connected between the negative input and ground. As the capacitor charges, it will trail the upgoing pulse from the phototransistor. When it catches the pulse, the output of the comparator 110 will be low, otherwise the output will be high. Therefore, the Q output of the flip-flop 122 will produce a series of logic ones when the slope of the output of the phototransistor is positive and will produce a series of logic zeros at all other times.

The Q output of the flip-flop 122 is fed into a 16 bit shift register 126, although shift registers having a greater bit capacity can be used. The outputs of the shift registers are fed into a NAND gate 128 and then inverted by an inverter 134 to produce a signal on line 22. Should any of the outputs of the shift register become a logic zero then the output of the inverter 134 will be a logic zero, thus indicating that a pulse has not been detected. When the shift register is filled with logic ones, the output of the inverter 134 will also be a logic one, thus indicating that a pulse has been detected. The capacity of the shift register 126 as well as the clocking rate for the flip-flop 122 and the shift register 126 is chosen so that base line noise, including 60 and 120 Hz noise, at the sensor is not detected as a pulse. In other words, for a pulse to be detected it must have a fairly high slope, such as that caused by a systolic beat.

With the reference to FIG. 3, the time delay 24 and the pulse shaper 28 will be described in detail. The output of the slope detector 20 appearing on line 22 is fed into a NAND gate 140. The other input to the NAND gate is received from the Q output of a flip-flop 142. The output of the NAND gate 140 provides a clock signal to the flip-flop 142 on line 148. The Q output of flip-flop 142 is fed to the D input of an up-counter 144 which has its reset grounded. The up-counter issues a signal every 16th pulse to reset the flip-flop 142. In this way, a time-delayed signal is issued on line 26 and fed into the pulse shaper 28. This time delay serves the purpose of providing a "dead time" interval where no spurious pulses, whether electronic or mechanical in origin, can be counted.

The pulse shaper 28 which is used to provide a pair of synchronized pulses on lines 30 and 32, comprises three flip-flops 150–152. Flip-flop 150 has its D input held high and is clocked by the signal on line 26. The Q output of flip-flop 150 is fed to the D input of flip-flop 151. The Q output of flip-flop 151 is fed to the D input of flip-flop 152 and also provides a signal on line 30. The Q output of the flip-flop 152 provides a signal on line 32 as well as a reset signal for flip-flop 150. Thus, the signals appearing on lines 30 and 32 are synchronized to further provide that no spurious pulses, electronic or mechanical, are allowed into the computation.

With reference to FIG. 4, a detailed description of the 60/t circuit 34 and the up-counter 38 will be provided. A conventional 12-bit up-counter 160 is enabled and reset by the signal on line 32. The output of the up-counter is a 12-bit number chosen to represent the time interval between reset times. This number is fed via lines 162 into a latch 164 which is clocked at a rate determined by the signal on line 30. The latch has its reset high so as to dump it contents into the divide-by-N ($\div$N) 168.

The divide-by-N is reset by the signal appearing on line 32 and is appropriately clocked by a signal on line 167 to produce at its output, a digital signal having a frequency equal to the number of heart beats per minute. Thus, it can be seen that the 60/t circuitry takes the time interval between systolic beats, and converts this time interval into a digital signal indicative of the number of heart beats per minute. This signal, which appears on line 36, is used to clock an up-counter 38 which is reset between detected beat intervals by the signal on line 32. The output of the up-counter is a 12-bit binary number, D11 through D0, which appears on lines 40. The output of the up-counter is fed via lines 40 to the multiplexer 46. At the same time bits D7 through D2 from the up-counter are fed into the holding registers 48 and the compare 54.

Figure 5:
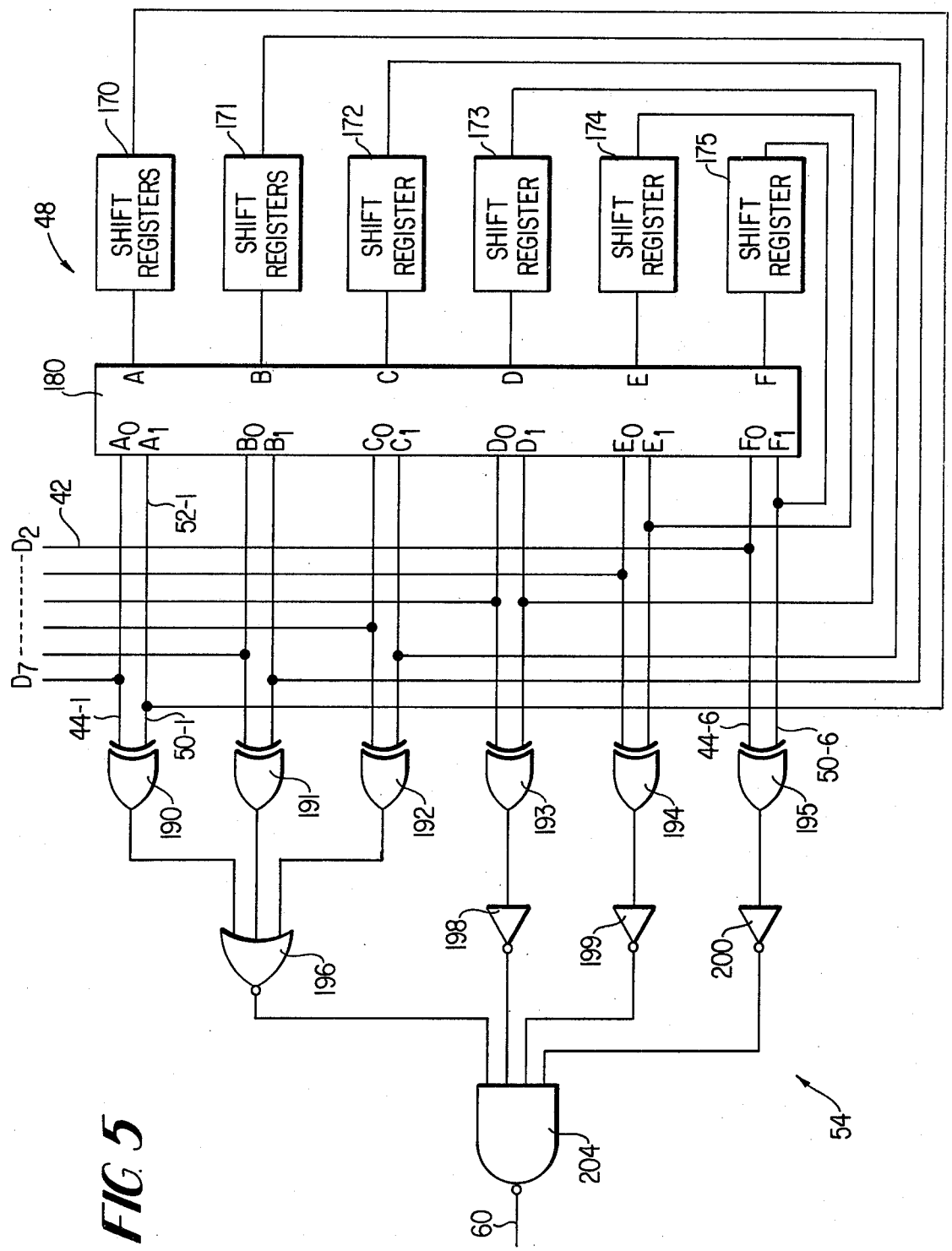
FIG. 5 is a block circuit diagram showing the holding registers and the compare.

With reference to FIG. 5, the details of the holding registers 48 and the compare 54 will now be described. Bits D7–D2 from the output of the up-counter 38 are simultaneously fed into the inputs $A_o$ through $F_o$ of a multiplexer 180 and a series of exclusive OR gates 190 through 195 via lines 44-1 through 44-6. The outputs, A through F, of the multiplexer 180 are fed into a series of 10-bit shift registers 170 through 175. The outputs of the shift registers are fed to inputs of the exclusive OR gates 190 through 195 via lines 51–56, and to the inputs $A_1$ through $F_1$ of the multiplexer 180 via lines 52-1 through 52-6.

The shift registers 170 through 175 shift the incoming data received from the multiplexer 180 on a first-in first-out (FIFO) basis. The data is shifted through the shift registers at such a rate so that each of the data samples is presented for comparison by the compare 54 with the selected bits D7 through D2 from the up-counter 38.

The outputs of the exclusive OR gates 190 through 192 are fed to a NOR gate 196 the output of which is fed to the input of a NAND gate 204. The outputs of exclusive OR gates 193 through 195 are fed to the inputs of NAND gate 204 via inverters 198 through 200, respectively.

The exclusive OR gates 190 through 195 each issue a logic 1 when the inputs to those gates are different and issue a logic 0 when the inputs are the same. When the outputs of all of the exclusive OR gates 190 through 195 are low, the output of the NAND gate 204 is high, indicating that a valid comparison has been made. If any of the outputs from the exclusive OR gates is high then the output of the NAND gate 204 will be low, indicating that a valid comparison has not been made.

By way of example, assume that the output from the up-counter 38 is a binary number indicating that the heart rate is 72 beats per minute. The output, D11–D0, of the up-counter 38 in binary notation is 0000, 0100, 1000. As stated before, only bits D7–D2 are fed into the exclusive OR gates. In this case, binary bits 010010 will be fed, respectively, to the inputs 41-1 through 44-6 of the exclusive OR gates. Since the two least significant bits of the output from the up-counter 38 have been excluded from the comparison, the output of the up-counter 38 will compare favorably to samples stored in the shift registers which are in the range between 72 and 75 beats per minute. This is due to the fact that the bits D7 through D2 for each of those numbers are the same as bits D7 through D2 for the number 72. A specific comparison range, obtained by excluding the two least significant bits, has been described. It is to be understood that the comparison range as well as the percentage difference between the numbers within the range may be increased by excluding a greater number of least significant bits. Further, the comparison range and the percentage difference may be narrowed by not excluding any least significant bits so that the percentage difference between samples is reduced to zero.

Returning now to FIG. 1, the compare signal on line 56 indicates that a valid comparison has been made. This signal provides a pulse to advance the up-counter 58. When the up-counter advances at least two, but typically three, units, it issues a latch signal on line 60 to latch the data previously stored in the latch 62, to appear on display 76. The multiplexer 46 is of conventional design, and may include a series of multiplexers designated as model number 4053 and manufactured by National Semiconductor, Inc., Santa Clara, Calif. Likewise the latch is of conventional design and may include a number of BCD-to-seven segment conversion devices. One such device is model number 4543, again, manufactured by National Semiconductor, Inc. The display 76 is typically of the type which converts the output of the latch 62 to an eye-readable array of integers. One such device is model number 741 manufactured by Beckman Instruments, Inc., Fullerton, Calif. Although there are numerous variations in the timing scheme used to clock the various components of the subject invention, excellent results have been obtained using the following clock rates:

512 Hz for the flip-flop 122 in the modulator and shift register 126 in the slope detector.

16 Hz to the up-counter 144 in the time delay.

32,768 Hz to the flip-flop 151 in the pulse shaper.

128 Hz to the up-counter 160 and 7680 Hz to the divide-by-N 168 in the 60/t circuit 34.

16,384 Hz to the shift registers 170–175 in the holding registers 48.

Figure 6:
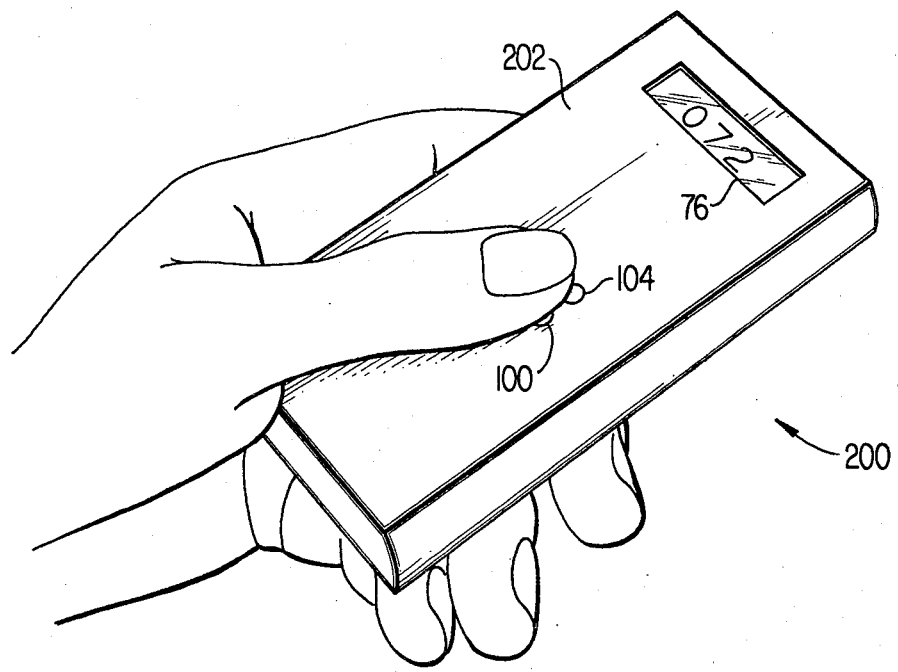
FIG. 6 is a perspective view of the hand-held embodiment of the subject cardiotachometer.

With reference to FIG. 6, a hand-held version of the unified, self-contained cardiotachometer with digital readout is generally designated as 200. The device comprises a unitized housing 202 shaped for convenient placement within the palm of the user. The light emitting diode 100 and the phototransistor 104 are positioned on the housing so as to receive the thumb of the user. In this way systoles are detected. The cardiotachometer circuitry, described hereinbefore, is mounted within the housing 200. The output of the phototransistor 104 is fed to the cardiotachometer circuitry, wherein it is processed and read out on the display 76 which is positioned on the housing for easy reading by the user.

Figure 7:
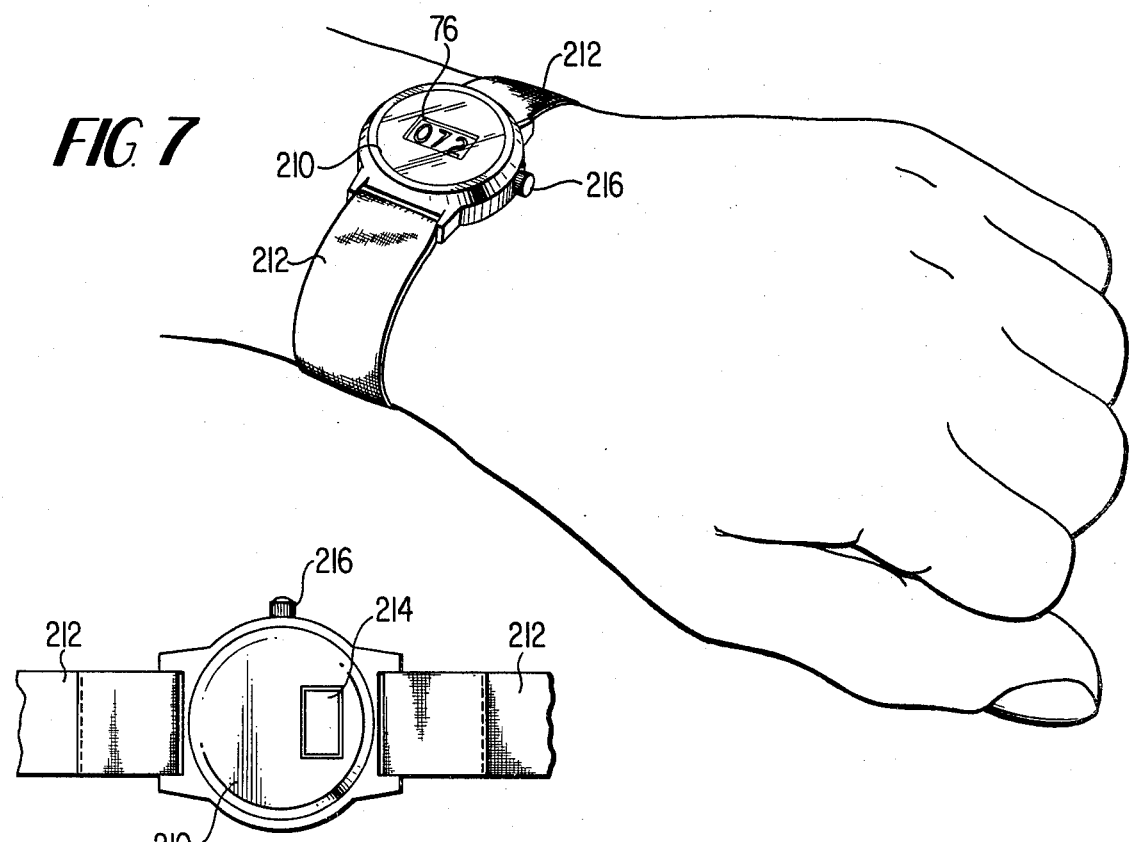
FIG. 7 is a perspective view of the subject cardiotachometer in the form of a wrist watch.
Figure 8:
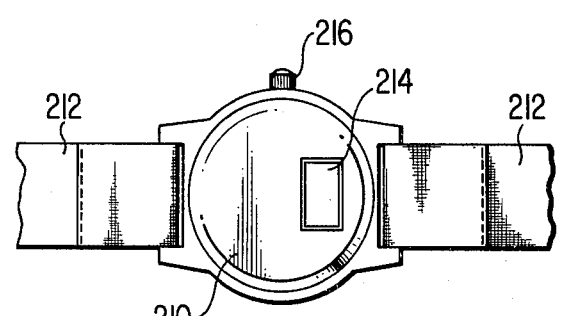
FIG. 8 is a schematic rear view of the cardiotachometer of FIG. 7.

The cardiotachometer of the subject invention being mounted in a wrist watch is shown in FIGS. 7 and 8. In this embodiment the cardiotachometer circuitry is mounted in a watch housing 210 which is secured to the wrist of the user by straps 212. The sensor, which is a piezoelectric transducer 214, is secured to the back of the housing 210 and detects systoles through the wrist of the user. A push button switch 216 is provided to select the function (heart rate, time of day, or elapsed time) to be displayed on the display 76.

Obviously many modifications and variations of the present invention are possible in light of the above teachings, and it is contemplated that the subject invention may be implemented through the use of discrete components or an integrated circuit chip. It is further comtemplated that an integrated circuit chip having complimentary-metal-oxide-silicon (CMOS) circuits may be used to configure the present invention, and that a remote sensor may be contained in a housing separate from that containing the remainder of the device. It is, therefore, to be understood that within the scope of the appended claims, the invention may be practiced otherwise and as specifically described.

What is claimed is:

1. A cardiotachometer for indicating heart rate of a user in beats per minute, said cardiotachometer comprising:

means, responsive to the heart beats of said user for producing a heart rate signal having portions representative of the beats per minute of said user's heart;

means for storing the portions of said heart rate signal;

means for comparing each of said stored portions with the most recent portion of said heart rate signal;

means for issuing a display signal when at least two of the comparisons in said comparing means is made between portions within a predetermined comparison range; and means, responsive to said display signal, for displaying said most recent portion of said heart rate signal in eye-readable format wherein heart rate in beats per minute is indicated.

2. The cardiotachometer of claim 1, wherein said at least two is three.

3. The cardiotachometer of claim 1 further including time delay means for removing spurious pulses.

4. A cardiotachometer for indicating heart rate of a user in beats per minute, said cardiotachometer comprising:

interval means, responsive to the heart beats of said user, for producing an interval signal having portions indicative of the time interval between said beats;

means for converting each portion of said interval signal into a heart rate signal having portions representative of the beats per minute of said user's heart;

means for storing the portions of said heart rate signal;

means for comparing each of said stored portions with the most recent portion of said heart rate signal;

means for issuing a display signal when at least two of the comparisons in said comparing means are made between portions within a predetermined percentage of each other; and means, responsive to said display signal, for displaying said most recent one of said plurality of signals in eye-readable format wherein heart rate in beats per minute is indicated.

5. The cardiotachometer of claim 4, further comprising sensor means, adapted to contact the skin of said user, for producing an electrical signal indicative of the heart beats of said user, and interconnect means for conveying said electrical signal for use by said interval means.

6. The cardiotachometer of claim 4 further including time delay means for removing spurious pulses.

7. The cardiotachometer of claim 4, further comprising means for producing a signal indicative of time-of-day for display by said displaying means.

8. The cardiotachometer of claim 4, further comprising means for producing a signal indicative of elapsed time for display by said displaying means.

9. A cardiotachometer for indicating heart rate in beats per minute of a user, said cardiotachometer comprising:

sensor means, adapted to contact the skin of said user, for producing an electrical signal inidicative of the heart rate of said user;

means for converting said electrical signal into first and second digital signals;

means responsive to said first and second digital signals for producing a third digital signal having a varying frequency representative of the number of heart beats per minute;

converting means for converting said third digital signal into a plurality binary number signals;

storing means for storing each of said binary number signals;

means for comparing each of said stored binary number signals with the most recent binary number signal from said converting means to determine if a plurality of compared signals are within a predetermined comparison range of each other; and means for displaying said most recent binary number signal when said plurality of compared signals are within said predetermined percentage of each other.

10. The cardiotachometer of claim 9, wherein said comparison range is determined by the number of least significant bits excluded from each of said stored and most recent binary number signals.

11. The cardiotachometer of claim 9, wherein said sensor means comprises a pressure transducer.

12. The cardiotachometer of claim 9, wherein said sensor means comprises a light source, and a photocell responsive to variations in light intensity reflected off of the capillary bed within the skin of said user, for producing a voltage signal representative of the heart rate of said user.

13. The cardiotachometer of claim 9, wherein said sensor means detects systolic beats in order to produce said electrical signal.

14. The cardiotachometer of claim 9, wherein said third digital signal producing means comprises counting means for producing an interval signal representing the time interval between heart beats, and dividing means responsive to said interval signal for producing said third digital signal.

15. The cardiotachometer of claim 14, wherein said producing means includes a latch for holding said interval signal before it is fed to said dividing means.

16. The cardiotachometer of claim 15, wherein said dividing means is a divide-by-N device.

17. The cardiotachometer of claim 9, wherein said converting means comprises an up-counter.

18. The cardiotachometer of claim 9, wherein said storing means comprises shift register means.

19. The cardiotachometer of claim 9, wherein said plurality of binary number signals each comprises a plurality of bits, and said storing means comprises a plurality of shift registers, each for receiving a particular bit of each binary number signal.

20. The cardiotachometer of claim 9, wherein said comparing means includes an exclusive OR gate for receiving said stored binary number signals and said most recent binary number signal.

21. The cardiotachometer of claim 19, wherein said comparing means further includes means for excluding at least one of the least significant bits of each of said binary number signals from being compared.

22. The cardiotachometer of claim 9, wherein said comparing means includes means for issuing a compare signal each time said compared signals are within a predetermined percentage of each other, and wherein said displaying means includes means for issuing a display signal after receiving a plurality of said compare signals.

23. The cardiotachometer of claim 22, wherein said plurality of compare signals is three.

24. The cardiotachometer of claim 9, wherein said displaying means includes latch means for holding said most recent binary number signal prior to display, and means for displaying the contents of said latch means as an array of integers.

* * * * *